United States Patent
Tsukada et al.

(10) Patent No.: US 11,337,621 B2
(45) Date of Patent: May 24, 2022

(54) LACTATE WORKING THRESHOLD-ESTIMATING DEVICE AND LACTATE WORKING THRESHOLD-ESTIMATING METHOD

(71) Applicants: NIPPON TELEGRAPH AND TELEPHONE CORPORATION, Tokyo (JP); THE UNIVERSITY OF TOKYO, Tokyo (JP)

(72) Inventors: Shingo Tsukada, Atsugi (JP); Nahoko Kasai, Atsugi (JP); Hiroshi Nakashima, Atsugi (JP); Hideo Hatta, Tokyo (JP)

(73) Assignees: NIPPON TELEGRAPH AND TELEPHONE CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 524 days.

(21) Appl. No.: 16/330,988

(22) PCT Filed: Sep. 8, 2017

(86) PCT No.: PCT/JP2017/032497
§ 371 (c)(1),
(2) Date: Mar. 6, 2019

(87) PCT Pub. No.: WO2018/047945
PCT Pub. Date: Mar. 15, 2018

(65) Prior Publication Data
US 2019/0231225 A1    Aug. 1, 2019

(30) Foreign Application Priority Data

Sep. 9, 2016 (JP) .............................. JP2016-176757

(51) Int. Cl.
*A61B 5/11* (2006.01)
*A61B 5/00* (2006.01)
(Continued)

(52) U.S. Cl.
CPC ............ *A61B 5/112* (2013.01); *A61B 5/1038* (2013.01); *A61B 5/1123* (2013.01); *A61B 5/22* (2013.01);
(Continued)

(58) Field of Classification Search
CPC ..... A61B 5/112; A61B 5/1038; A61B 5/1123; A61B 5/22; A61B 5/4866; A61B 2503/10;
(Continued)

(56) References Cited

U.S. PATENT DOCUMENTS

| 4,736,312 A | 4/1988 | Dassler et al. |
| 2007/0010751 A1 | 1/2007 | Amano et al. |

(Continued)

FOREIGN PATENT DOCUMENTS

| JP | 06-090043 B | 11/1994 |
| JP | 4752646 B2 | 8/2011 |

(Continued)

OTHER PUBLICATIONS

Matthew L. Goodwin et al., "Blood Lactate Measurements and Analysis during Exercise: A Guide for Clinicians", Journal of Diabetes Science and Technology, vol. 1, Issue 4, Jul. 2007.
(Continued)

*Primary Examiner* — Devin B Henson
(74) *Attorney, Agent, or Firm* — Harness, Dickey & Pierce, P.L.C.

(57) ABSTRACT

A lactate working threshold-estimating device includes: an acquiring unit configured to acquire information on a gait of a person whose lactate working threshold value is to be
(Continued)

estimated from a sensor installed on the person; and an estimating unit configured to estimate the lactate working threshold value of the person on the basis of the acquired information.

5 Claims, 10 Drawing Sheets

(51) Int. Cl.
*A61B 5/103* (2006.01)
*A63B 24/00* (2006.01)
*A61B 5/22* (2006.01)
*A61B 5/389* (2021.01)

(52) U.S. Cl.
CPC .......... *A61B 5/389* (2021.01); *A61B 5/4866* (2013.01); *A61B 2503/10* (2013.01); *A61B 2562/0247* (2013.01); *A63B 24/0062* (2013.01); *A63B 2220/56* (2013.01)

(58) Field of Classification Search
CPC ............ A63B 24/0062; A63B 2220/50; A63B 2220/56
See application file for complete search history.

(56) References Cited

U.S. PATENT DOCUMENTS

| | | |
|---|---|---|
| 2007/0179350 A1 | 8/2007 | Nadeau |
| 2016/0000635 A1 | 1/2016 | Miyake |
| 2016/0143579 A1* | 5/2016 | Martikka ............. A61B 5/0245 600/301 |
| 2017/0188894 A1* | 7/2017 | Chang .................... G16H 50/30 |

FOREIGN PATENT DOCUMENTS

| | | |
|---|---|---|
| JP | 2014-128464 A | 7/2014 |
| WO | WO-2016/039241 A1 | 3/2016 |

OTHER PUBLICATIONS

Hideo Hatta, "How to think about lactic acid", physical fitness science, 59, 8-10, 2010 (with partial translation).

International Search Report for International Patent Application No. PCT/JP2017/032497 (in Japanese), dated Oct. 31, 2017, with English translation thereof.

* cited by examiner

LACTATE WORKING THRESHOLD-ESTIMATING DEVICE AND LACTATE WORKING THRESHOLD-ESTIMATING METHOD

CROSS-REFERENCE TO RELATED APPLICATIONS

This application is a 371 U.S. National Stage of International Application No. PCT/JP2017/032497, filed on Sep. 8, 2017, which claims priority to Japanese Patent Application No. 2016-176757, filed in Japan on Sep. 9, 2016. The contents of both of the above applications are incorporated herein by reference.

TECHNICAL FIELD

The present invention relates to a technique for estimating a lactate working threshold value.

BACKGROUND ART

In the related art, techniques for measuring a walking or running gait have been sought in various fields such as health promotion, prevention of accidents caused by exercise, science experiments, sports science, sports physiology, medicine, and rehabilitation medicine. However, the measurement of a gait in the related art is performed on a special indoor track including floor reaction gauges under the floor. Thus, it was difficult to perform measurement during competitions, daily life, and training.

Also, it is difficult to measure the entire running because of the constraint that a reaction meter is installed in only a part of a runway and there is a demand for a technique for continuously measuring a gait during a competition.

With regard to a gait, it has not become general knowledge that movement of the lower limbs in walking and running, the temporal relationship from coming in contact with the ground of the portion of the heel to coming in contact with the ground of the ball of the foot (a protrusion of the toes), and changes in a floor reaction force over time are important for research on running, improvement of running speed, efficiency of exercise, and the like. In endurance-based exercises such as a marathon, a middle distance race, and a bicycle race, metabolic ability and technology that allow each player to exert maximum power which can sustain muscle activity to the goal are required. For example, an exercise intensity representing a significant increase in blood lactate concentration is referred to as a "lactate working threshold value" and is widely used in the fields of strengthening athletes and sports science as an indicator representing endurance of athletes.

CITATION LIST

Patent Literature

[Non-Patent Literature 1]
Matthew L. Goodwin, M. A., James E. Harris, M. Ed., Andres Hernandez, M. A., and L. Bruce Gladden, Ph.D., "Blood Lactate Measurements and Analysis during Exercise: A Guide for Clinicians," Journal of Diabetes Science and Technology, Vol. 1, Issue 4, July 2007
[Non-Patent Literature 2]
Hideo HATTA, "How to think of lactic acid," The Japanese Journal of Physical Fitness and Sports Medicine 59, 8 to 10, 2010

SUMMARY OF INVENTION

Problem to be Solved by the Invention

Although a lactate working threshold value is a highly reliable parameter indicating endurance of an athlete, it has the following two problems and thus has not yet become widespread in general sports. The first problem is that a blood sample is required to measure a blood lactate value. The second problem is that it is necessary to use a measuring device such as an ergometer or a power meter to measure output power and no method has been established to measure an output during walking or running except for a bicycle race in which an output power value can be calculated directly from the torque at the time of the cranking operation. In this way, in the related art, there was a problem in that it was not possible to estimate a lactate working threshold value in a state close to an actual movement environment.

The present invention was made in view of the above-described circumstances, and an objective of the present invention is to provide a technique capable of estimating a lactate working threshold value in a state close to an actual movement environment.

Means for Solving the Problem

A lactate working threshold-estimating device according to an aspect of the present invention includes: an acquiring unit configured to acquire information on a gait of a person whose lactate working threshold value is to be estimated from a sensor installed on the person; and an estimating unit configured to estimate the lactate working threshold value of the person on the basis of the acquired information.

According to an aspect of the present invention, in the lactate working threshold-estimating device, the estimating unit may estimate the lactate working threshold value on the basis of the information including at least one of a plantar pressure and a floor reaction force during walking movement or during running movement.

According to an aspect of the present invention, in the lactate working threshold-estimating device, the estimating unit may estimate the lactate working threshold value on the basis of the information including at least one characteristic amount among a stride, a pitch, a foot/ground contact time, a plantar pressure distribution, a difference between right and left gaits in a plantar pressure, and dispersion for each step during walking movement or during running movement.

According to an aspect of the present invention, in the lactate working threshold-estimating device, the estimating unit may estimate the lactate working threshold value on the basis of a change point of an amount of increase/decrease of the stride or the pitch in accordance with a change in exercise intensity.

According to an aspect of the present invention, in the lactate working threshold-estimating device, the estimating unit may estimate the lactate working threshold value on the basis of the information including at least one of a plantar pressure and a floor reaction force in accordance with a change in exercise intensity during walking movement or during running movement.

According to an aspect of the present invention, the lactate working threshold-estimating device may include at least one of a mechanism for correcting a fluctuation in sensitivity of the sensor and an adjustment mechanism for a measuring range of a pressure.

According to an aspect of the present invention, the lactate working threshold-estimating device may further include an output unit configured to feed back a result indicating an interrelationship between the lactate working threshold value and a current or previous exercise intensity to at least the person.

A lactate working threshold-estimating method according to an aspect of the present invention includes: acquiring information on a gait of a person whose lactate working threshold value is to be estimated from a sensor installed on the person; and estimating the lactate working threshold value of the person on the basis of the acquired information.

Advantageous Effects of Invention

According to the present invention, it is possible to estimate a lactate working threshold value in a state close to an actual movement environment.

DESCRIPTION OF EMBODIMENTS

An embodiment of the present invention will be described below with reference to the drawings.

[Outline]

When a walking or running intensity, for example, a walking speed or a running speed, gradually increases, a gait changes along with the increase in exercise intensity. For example, differences between right and left gaits or variations of a stride, a pitch, and a foot/ground contact time decrease. This is a phenomenon caused by a physiological adaptation phenomenon in which a body movement method is optimized toward a more efficient state to cope with an increase in exercise intensity. On the other hand, when an exercise intensity is low, so-called "play" occurs in a gait and efficiency is poor. When an exercise intensity is higher than a lactate working threshold value, sugar oxidation, which is easier to use, is mainly used instead of metabolism mainly based on sustained lipid oxidation in an energy metabolism pathway of a body. However, an amount of sugar to be stored is not large and the subjective tightness increases. Thus, it is difficult to sustain the movement for a long time. For this reason, a motion in which power consumption is minimized as much as possible through the above-described optimization of running and an unnecessary output is minimized occurs. As a result, a stride, a pitch, and a foot/ground contact time associated with a gait change at about an exercise intensity indicating a lactate working threshold value. It has also been observed that a difference between floor reaction forces of right and left legs, the dispersion of each parameter for each step, and the like, which have individual differences, tend to decrease. Furthermore, cases in which the trajectory of a pressure center (center of gravity) of the sole during ground contact also changes in the vicinity of a lactate working threshold value have also been observed.

In a region in which an exercise intensity exceeding a lactate working threshold value is high, while the above-described optimization reaches the limit, the characteristics such as an increase in pitch and reduction of foot/ground contact time for the purpose of further increasing an exercise intensity (running speed) are also observed. An in-body energy metabolism state can be determined to be a low intensity state lower than a lactate working threshold value, a state of the lactate working threshold value, or a high intensity region having a value exceeding the lactate working threshold value on the basis of a change in data associated with gait, which is caused by the above-described physiological adaptive reaction, particularly, the above-described change in correlation between the exercise intensity and the characteristic amount (also referred to as an "inflection point" and a "change point"). In the present invention, a change in gait caused by a physiological adaptive reaction accompanying a change in intensity of walking or running is estimated using a wearable sensor configured to measure a plantar pressure and acceleration and a lactate working threshold value is estimated on the basis of the estimated result.

[Details]

A machine and a device to be used in the embodiment will be first described with reference to FIGS. 1A to 1D.

As illustrated in FIGS. 1A to 1D, in the embodiment, a plurality of pressure sensors 1 to 3, a transmitter 4, a motion sensor 5, a receiving device 6, and an estimating device 7 are used.

Figure 1A:
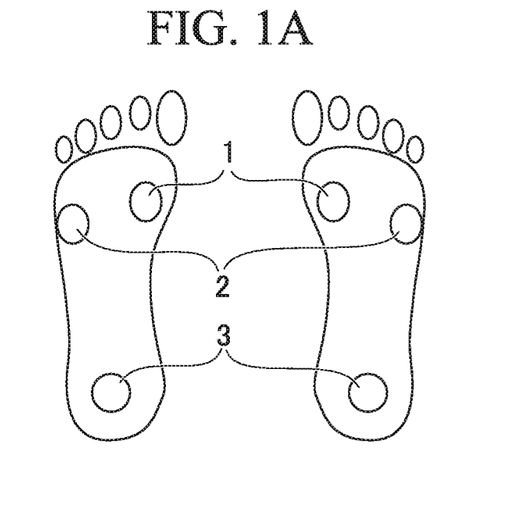
FIG. 1A is a diagram explaining a plurality of pressure sensors used in an embodiment.

The pressure sensors 1 to 3 are installed on a plantar portion of a testee. Here, the testee is a person whose lactate working threshold value is to be estimated. The pressure sensor 1 is installed at a center of a pressure distribution of the ball of the foot of the testee. The pressure sensor 2 is installed at a center of a pressure distribution of lateral ball of the foot of the testee. The pressure sensor 3 is installed at a center of a pressure distribution of a heel portion of the testee. In the heel portion, it is desirable that the pressure sensor 3 be disposed at a portion at which a pressure of the heel portion is concentrated such as a portion immediately below the calcaneal tuberosity inside and outside the protrusion portion. It should be noted that the pressure sensors 1 to 3 are preferably disposed on symmetrically both feet. The pressure sensors 1 to 3 estimate a pressure applied to the plantar portion of the testee.

Figure 1B:
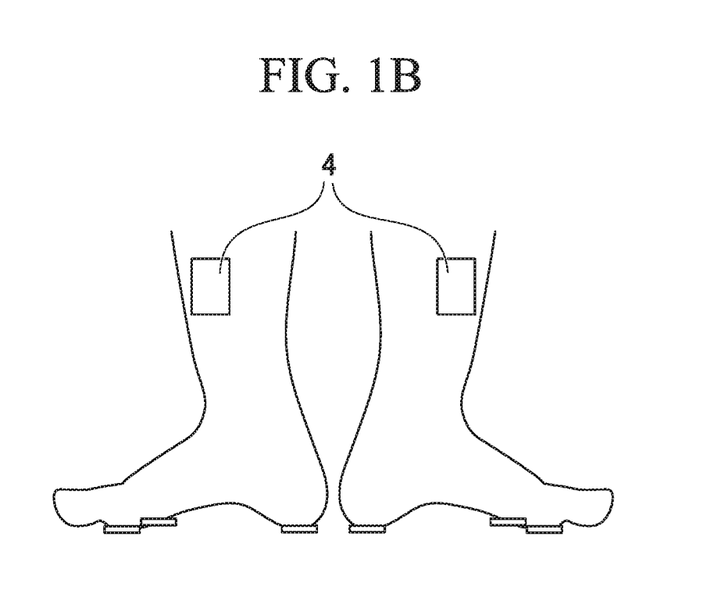
FIG. 1B is a diagram explaining a transmitter used in the embodiment.

The transmitter 4 transmits pressure information estimated by the pressure sensors 1 to 3.

Figure 1C:
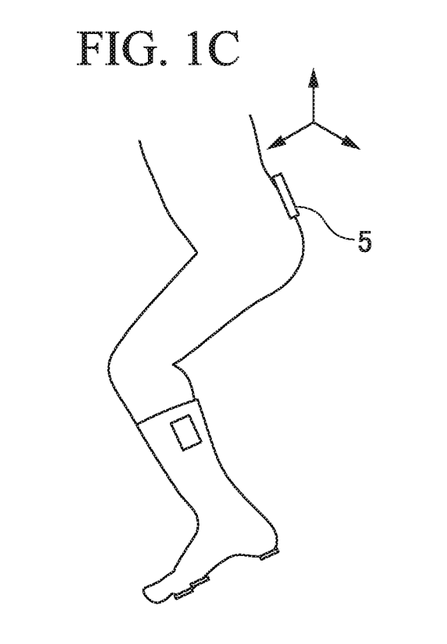
FIG. 1C is a diagram explaining a motion sensor used in the embodiment.

The motion sensor 5 is installed on the testee to measure a gait of walking or running of the testee. The motion sensor 5 is installed on at least one place of the lumbar plate, the body trunk, the four limbs, and the head. More preferably, the motion sensor 5 is installed between the waist portion and the pelvic portion. The motion sensor 5 acquires information on motion of the testee (hereinafter referred to as "motion information"). The motion information is, for example, a speed, acceleration, a gyro, an orientation, and the like.

Figure 1D:
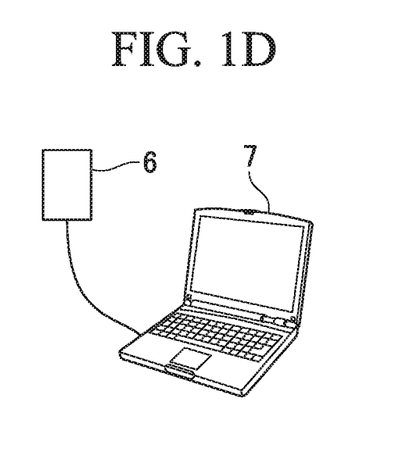
FIG. 1D is a diagram explaining a receiving device and an estimating device used in the embodiment.

The receiving device 6 receives pressure information transmitted from the transmitter 4 and the motion information acquired by the motion sensor 5.

The estimating device 7 is constituted using an information-processing device such as a personal computer. The estimating device 7 estimates a lactate working threshold value of the testee on the basis of the information received by the receiving device 6 and feeds back a relationship between the lactate working threshold value and a current exercise intensity as the estimated result to the testee or an observer.

Figure 2A:
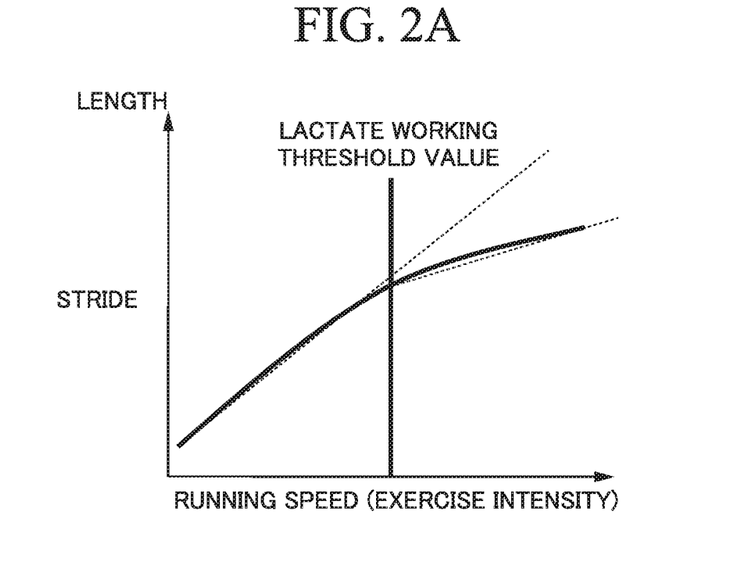
FIG. 2A is a diagram describing the concept of lactate working threshold value estimation on the basis of a relationship between a stride and a running speed (exercise intensity).
Figure 2B:
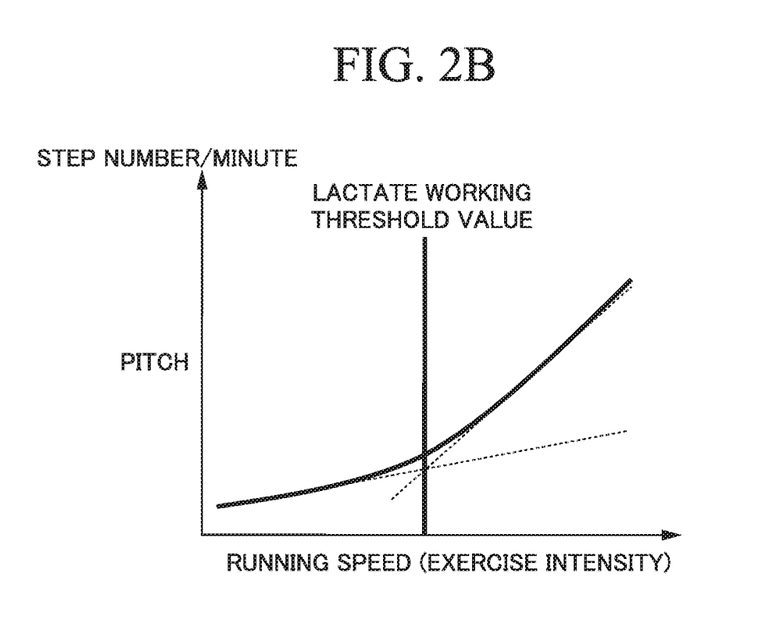
FIG. 2B is a diagram describing the concept of lactate working threshold value estimation on the basis of a relationship between a pitch and a running speed (exercise intensity).

FIGS. 2A and 2B are diagrams describing the concept of lactate working threshold value estimation based on parameters of a gait.

FIGS. 2A and 2B illustrate the concept of estimation for two strides and two pitches serving as parameters of a gait. FIG. 2A illustrates a relationship between a stride and a running speed (exercise intensity) and FIG. 2B illustrates a relationship between a pitch (step number per minute) and a running speed (exercise intensity). The exercise intensity is a scale indicating a load exerted on a physical body. The exercise intensity is, for example, a running speed, a walking speed, an inclination of a runway or a walkway, a stair height, a stepping intensity of a stepper, and the like. FIGS. 2A and 2B illustrate a relationship between the parameters of the gait and the exercise intensity when the exercise intensity is a running speed.

When the stride is measured while increasing the running speed stepwise or continuously, as illustrated in FIG. 2A, it can be seen that the extension of the stride peaks and an increment of the stride is suppressed when an exercise intensity exceeds the lactate working threshold value. That is to say, it is possible to estimate the lactate working threshold value by investigating a running speed at which an increase width of the stride along with an increase in the running speed is equal to or less than a threshold value. For example, a threshold value is not determined at the time of measurement start but is estimated on the basis of a sharp change in increase of the stride. In this way, it is possible to estimate the lactate working threshold value by investigating a running speed at a point at which an increase width of the stride along with an increase in the running speed changes (hereinafter referred to as a "change point").

Likewise, as illustrated in FIG. 2B, it is shown that a pitch at a speed exceeding the lactate working threshold value significantly increases. That is to say, it is possible to estimate the lactate working threshold value by investigating a running speed at which an increase width in pitch or the stride along with an increase in the running speed is equal to or more than a threshold value. For example, a threshold value is not determined at the time of measurement start but is estimated on the basis of a sharp change in increase of the pitch. In this way, it is possible to estimate the lactate working threshold value by investigating a running speed at a change point with an increase width of the pitch along with an increase in the running speed.

The lactate working threshold value is not limited to estimation based on the change point when the running speed increases, that is, when the exercise intensity increases, as long as the lactate working threshold value is estimated on the basis of a change point of an interrelationship between the stride or a pitch and the exercise intensity. The lactate working threshold value may be estimated on the basis of a change point with a decrease width of the stride along with, for example, a decrease in the running speed, that is, a decrease in the exercise intensity or a change point at which the pitch descends gently.

To be specific, when the estimation is based on the change point of the stride along with the decrease in the running speed, it is possible to estimate the lactate working threshold value by detecting a running speed at which a decrease width of the stride is equal to or more than a threshold value. On the other hand, when the estimation is based on the change point of the pitch along with the decrease in the running speed, it is possible to estimate the lactate working threshold value by detecting a running speed at which a decrease width of the pitch is equal to or less than a threshold value.

In this way, it is possible to estimate the lactate working threshold value on the basis of an exercise intensity corresponding to a change point of an amount of increase/decrease (increase/decrease width) in the stride or the pitch in accordance with a change (increase/decrease) of the exercise intensity.

Figure 3A:
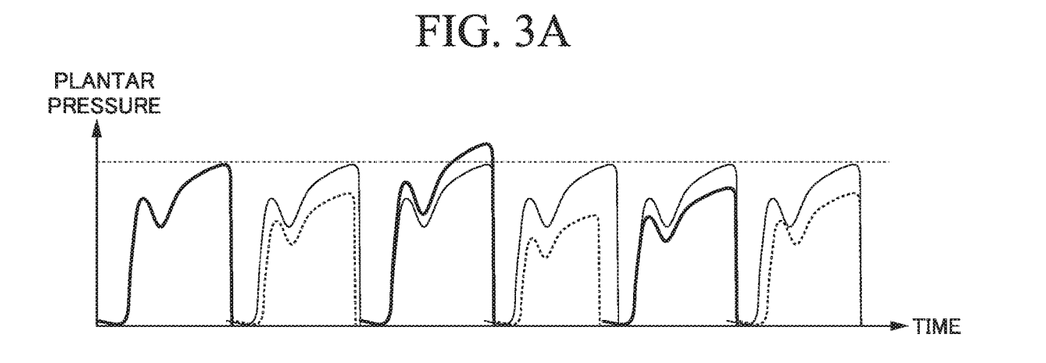
FIG. 3A is a diagram describing the characteristics of a plantar pressure during running at a speed (low intensity) lower than a lactate working threshold value in lactate working threshold value estimation based on a difference between right and left gaits and a difference in one step.
Figure 3B:
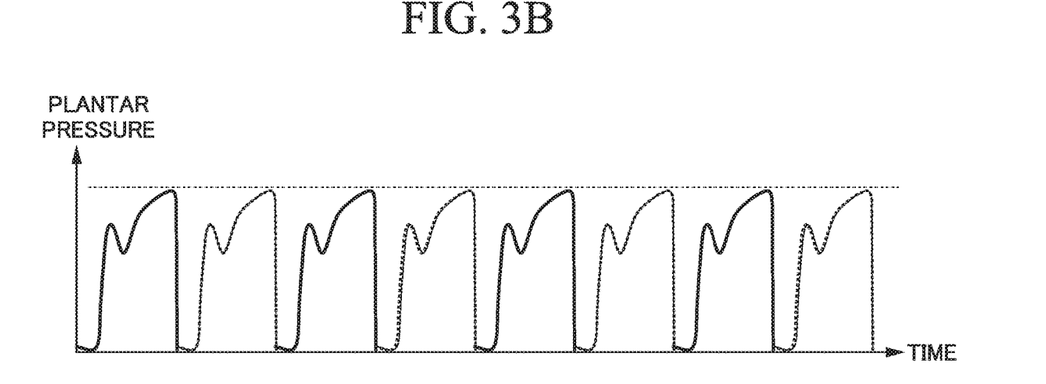
FIG. 3B is a diagram describing the characteristics of a plantar pressure during running of a lactate working threshold value in lactate working threshold value estimation based on a difference between right and left gaits and a difference in one step.

FIGS. 3A and 3B are diagrams describing the concept of lactate working threshold value estimation based on a difference between right and left of a gait or a difference in one step of the gait.

FIG. 3A is a diagram describing the characteristics of a plantar pressure at the time of running having a speed value lower than (having a lower intensity than that of) a lactate working threshold value and FIG. 3B is a diagram describing the characteristics of a plantar pressure at the time of running indicating the lactate working threshold value. In FIGS. 3A and 3B, a thick solid line represents the characteristics of a plantar pressure of a right foot, a dotted line represents the characteristics of a plantar pressure of a left foot, and a thin solid line represents the characteristics of a plantar pressure as a reference. In the walking and running at a speed lower than the lactate working threshold value, as illustrated in FIG. 3A, a difference between right and left of the gait or a fluctuation of a value for each step of the gait is seen in some places. On the other hand, as illustrated in FIG. 3B, the difference between right and left of the plantar pressure and the fluctuation (variation) of the value for each step of the plantar pressure are reduced when the exercise intensity is close to the lactate working threshold value. That is to say, it is possible to estimate the lactate working threshold value on the basis of a decrease in the difference between right and left of the plantar pressure or a decrease in variation (dispersion) of parameters of the gait. In this way, it is possible to estimate the lactate working threshold value on the basis of the change point of the difference between right and left of the plantar pressure or the change point of the dispersion of the plantar pressure of each step in accordance with a change in the exercise intensity.

Figure 4A:
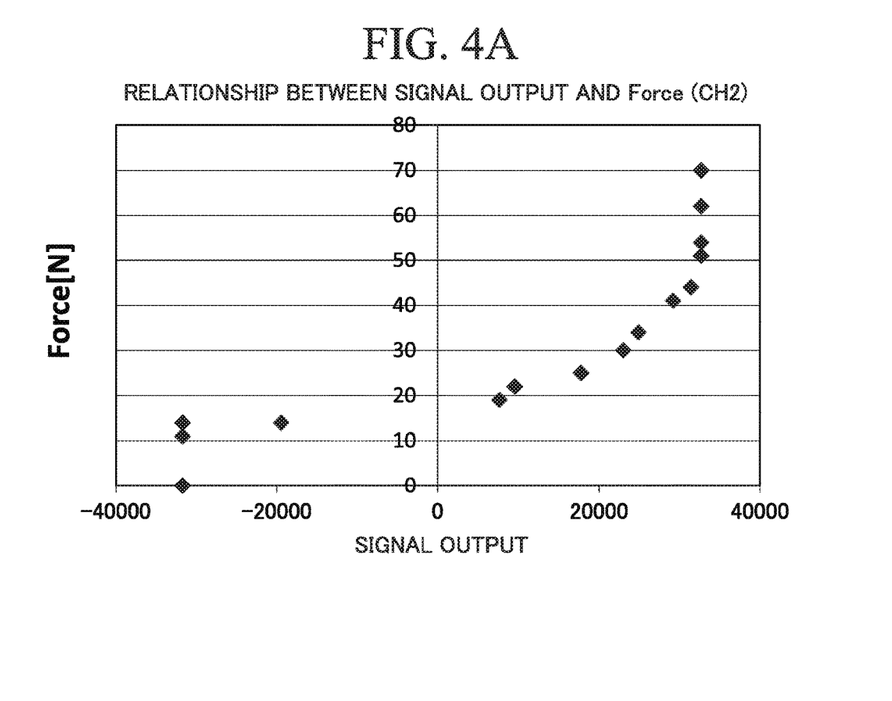
FIG. 4A is a diagram describing a relationship between plantar pressure sensors and a force.
Figure 4B:
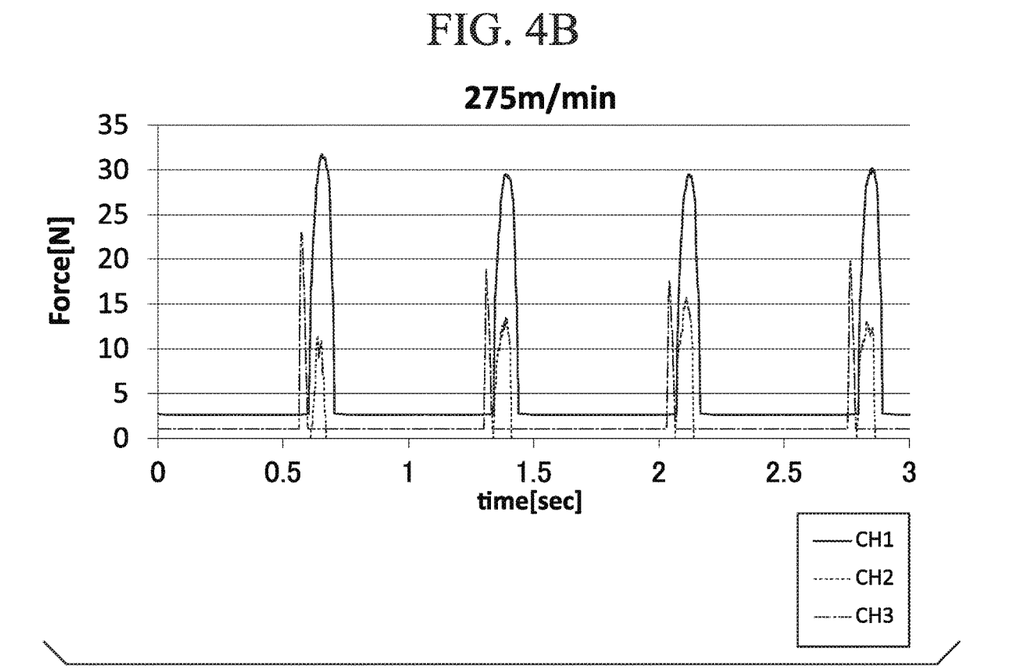
FIG. 4B is a diagram describing a relationship between pressures at a running speed in the vicinity of a lactate working threshold value.

FIGS. 4A and 4B are diagrams describing a relationship between plantar pressure sensors and a force and a relationship between pressures at a running speed in the vicinity of a lactate working threshold value.

FIG. 4A is a diagram describing the relationship between output of the plantar pressure sensors and the force. A output signal (absolute value) of a graph, that shows a relationship between a pressure and an output signal while applying the pressure of a force gauge to the pressure sensors 1 to 3 installed on the sole and changing the pressure of the force gauge, increases due to increases in pressure as illustrated in FIG. 4A. In this case, measurement was performed using a pressure region having a linear relationship. FIG. 4B is a diagram showing a time series graph of pressures of the ball CH1, the lateral ball CH2, and the heel portion CH3 at a running speed in the vicinity of a lactate working threshold value for each running speed 275 meter/minute. Due to a landing of the heel, a short pressure increase occurs in the order of the heel portion CH3, the lateral ball CH2, and the ball CH1 and the pressure remains in the ball CH1 to the end. In this way, movement of the plantar pressure is observed.

Figure 5A:
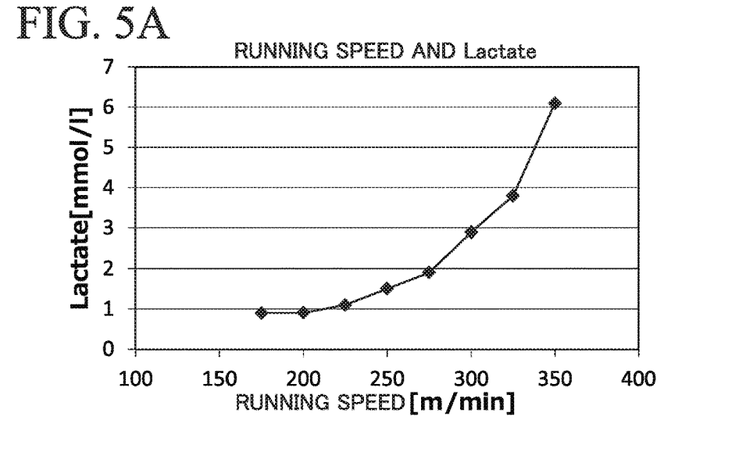
FIG. 5A is a diagram describing a relationship between a running speed and a blood lactate value.
Figure 5B:
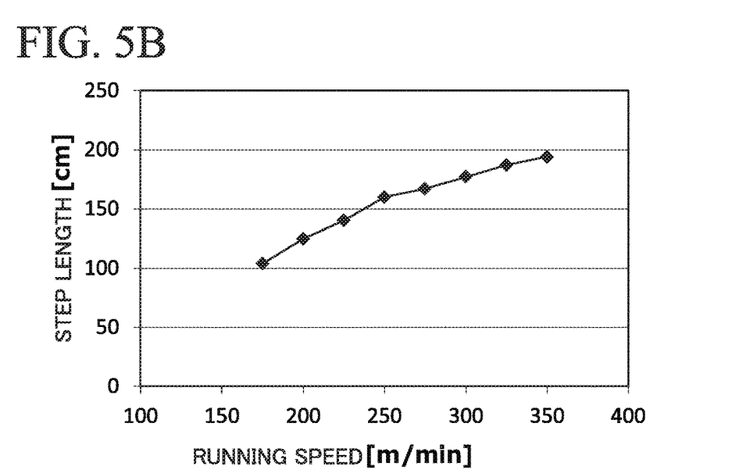
FIG. 5B is a diagram describing a relationship between a running speed and a step length (stride).
Figure 5C:
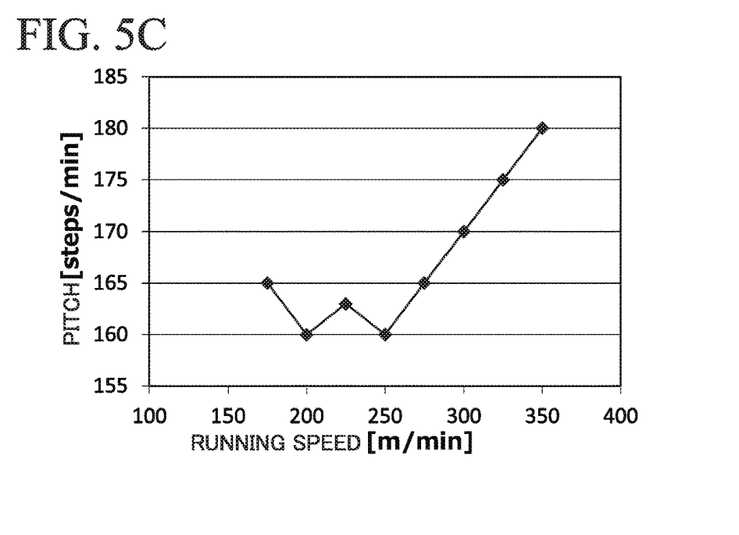
FIG. 5C is a diagram describing a relationship between a pitch (step number per minute) and a running speed.

FIGS. 5A to 5C are diagrams describing relationships with a running speed. FIG. 5A is a diagram describing a relationship between a running speed and a blood lactate value. FIG. 5A illustrates the results of measuring a blood lactate value by collecting a blood sample while increasing a running speed stepwise. It is conceivable that a lactic acid value rapidly increases from a running speed corresponding to a running speed of 250 to 300 meter/minute and a running speed corresponding to 275 meter/minute is a lactate working threshold value. FIG. 5B is a diagram describing a relationship between a running speed and a step length (stride). Referring to FIG. 5B, an increase width of a step length is reduced in the vicinity of the lactate working threshold value (corresponding to 275 meter/minute) and a relationship between a gait and the lactate working threshold value is illustrated. FIG. 5C is a diagram describing a relationship between a pitch (step number per minute) and a running speed. FIG. 5C illustrates a running speed increasing due to an increase in pitch in the vicinity of the lactate working threshold value (corresponding to 275 meter/minute).

Figure 6:
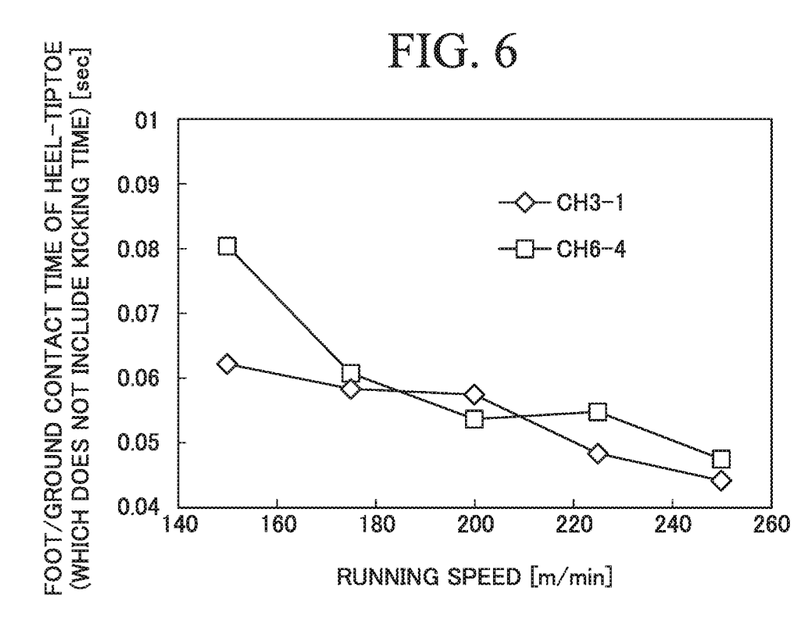
FIG. 6 is a diagram illustrating an example of a difference between right and left gaits observed at a running speed equal to or lower than a lactate working threshold value.

FIG. 6 is a diagram illustrating an example of a difference between right and left gaits observed at a running speed equal to or lower than a lactate working threshold value. In FIG. 6, lines CHs 1 to 3 represent a relationship between a foot/ground contact time of a tiptoe from a heel portion in a right foot and a running speed and lines CHs 4 to 6 represent a relationship between a foot/ground contact time of a tiptoe from a heel portion in a left foot and a running speed. Comparing the lines CHs 1 to 3 and the lines CHs 4 to 6, it can be seen that large differences between right and left gaits are observed at a low running speed, whereas differences between right and left gaits are reduced when a running speed increases toward the lactate working threshold value.

Figure 7A:
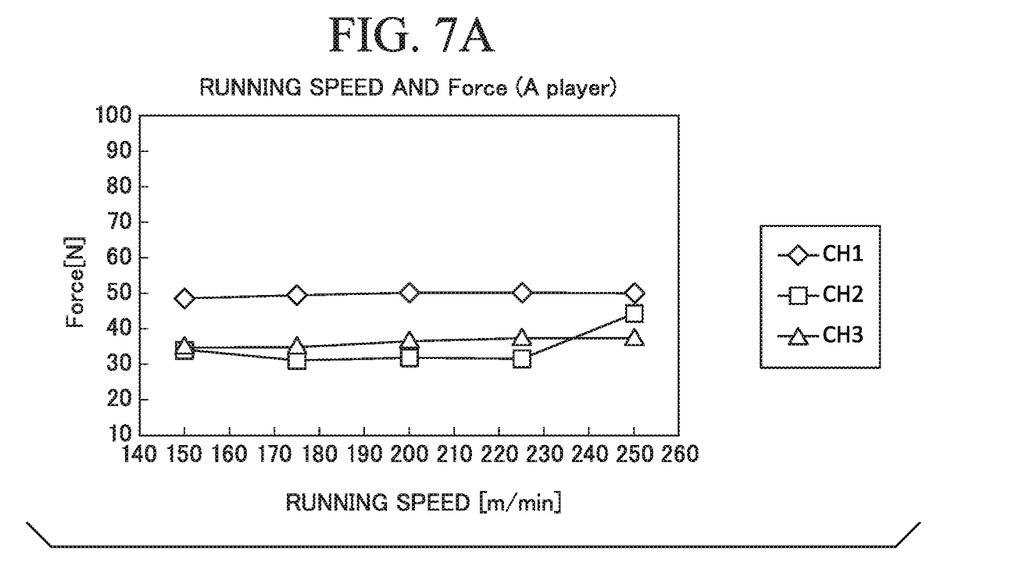
FIG. 7A is a diagram associated with an interrelationship between a running speed and pressures at three points on the sole of an athlete A.
Figure 7B:
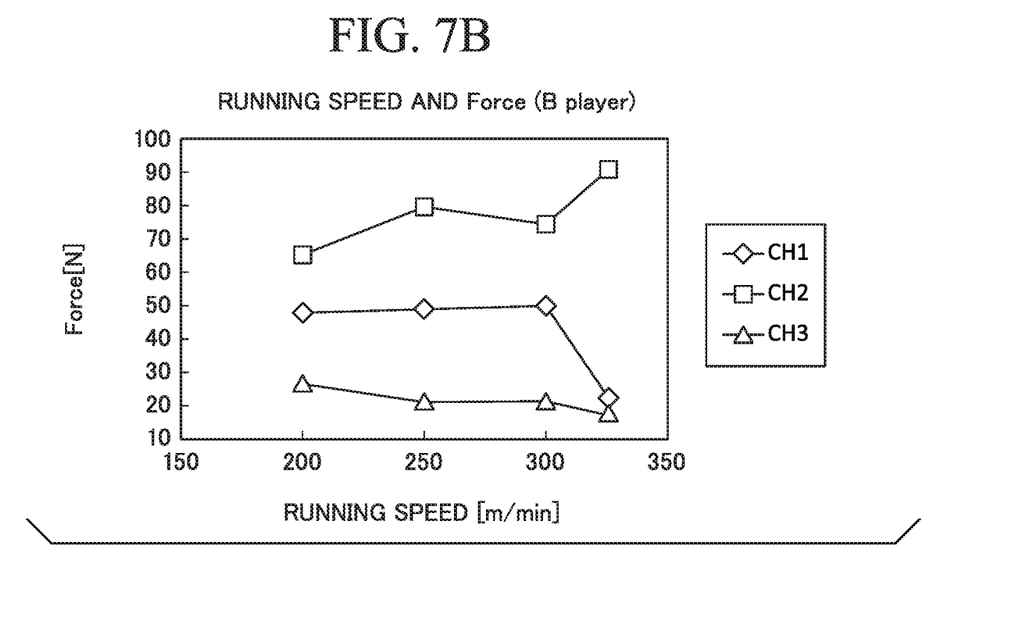
FIG. 7B is a diagram associated with an interrelationship between a running speed and pressures at three points on the sole of an athlete B.

FIGS. 7A and 7B are diagrams associated with an interrelationship between a running speed and a pressure at three points on the sole.

In FIGS. 7A and 7B, the results of two players (A player and B player) are illustrated. FIG. 7A illustrates the result of the A player and FIG. 7B illustrates the result of the B player. In FIGS. 7A and 7B, the line CH1 indicates a pressure of the heel portion, the line CH2 indicates a pressure of the lateral ball of the foot, and the line CH3 indicates a pressure of the ball of the foot. When attention is paid to a change in pressure in an inward/outward direction in front of the foot and an interrelationship between pressures of the lateral ball of the foot (line CH2) and the ball of the foot (line CH3) is viewed, in the case of the A player, the pressure is reversed from the ball of the foot (inside) to the lateral ball of the foot (outside) due to an increase in running speed. That is to say, the gait shifts to an external weighted. In other words, a pressure distribution of the sole changes and a center of gravity of the sole moves. There is also a similar tendency for the B player. In the data of the B player, there is a difference in displayed values of three points due to the characteristics of the sensor and it is necessary to correct this. In a change in Force value in accordance with a change in a running speed after correction, as in the case of the A player, a pressure of the ball portion of the foot slightly decreases in a high intensity region and a pressure of the lateral ball portion of the foot increases. In addition, a change of an absolute value showed the same tendency as a pattern of the A player.

Figure 8:
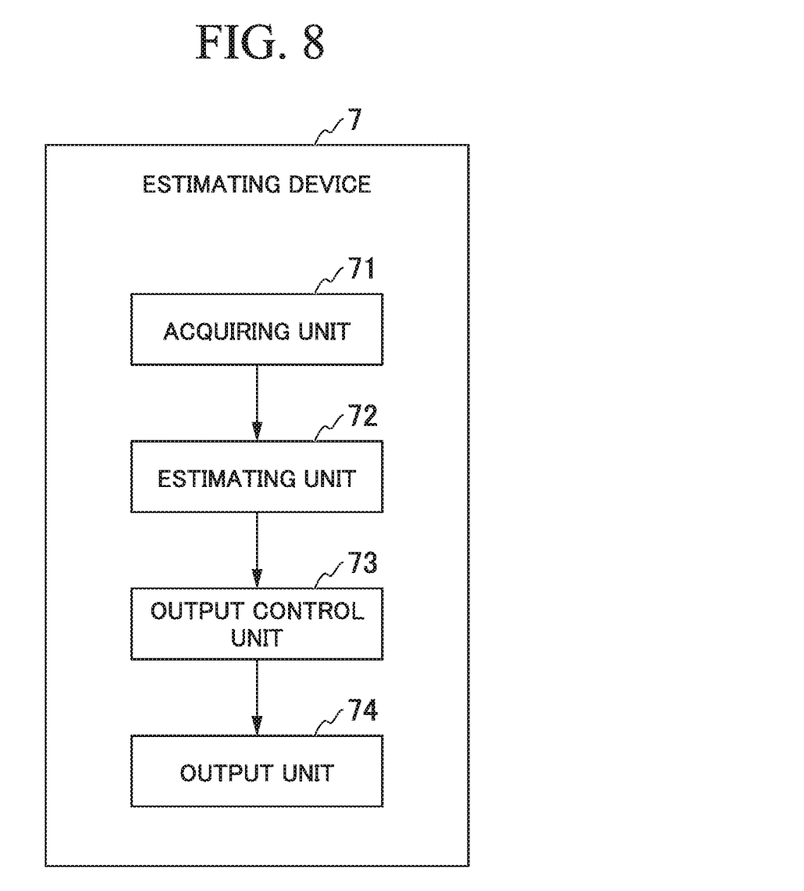
FIG. 8 is a schematic block diagram showing a functional constitution of the estimating device 7.

In this way, it is possible to estimate a lactate working threshold value on the basis of a change point of a pressure distribution of the sole along with a fluctuation of the exercise intensity FIG. 8 is a schematic block diagram showing a functional constitution of the estimating device 7.

The estimating device 7 includes a central processing unit (CPU), a memory, an auxiliary storage device, and the like which are connected through a bus and executes an estimation program. Through the execution of the estimation program, the estimating device 7 functions as a device which includes an acquiring unit 71, an estimating unit 72, an output control unit 73, and an output unit 74. It should be noted that all or some of functions of the estimating device 7 may be realized using hardware such as an application-specific integrated circuit (ASIC), a programmable logic device (PLD), a field-programmable gate array (FPGA), and the like. Furthermore, the estimation program may be recorded on a computer-readable recording medium. The computer-readable recording medium is, for example, a storage device such as a portable medium such as a flexible disk, a magneto-optical disk, a read-only memory (ROM), and a compact disc (CD)-ROM and a hard disk built in a computer system. In addition, the estimation program may be transmitted and received via an electric telecommunication line.

The acquiring unit 71 acquires pressure information acquired through the pressure sensors 1 to 3 and motion information (information on a gait) acquired through the motion sensor 5. The acquiring unit 71 outputs the acquired information to the estimating unit 72.

The estimating unit 72 estimates a lactate working threshold value of the testee on the basis of the information output from the acquiring unit 71. The specific processing of the estimating unit 72 will be described later. An evaluation unit 102 outputs the estimated result to the output control unit 73.

The output control unit 73 controls the output unit 74 on the basis of the estimated result of the estimating unit 72. For example, the output control unit 73 outputs a relationship between the estimated result and a current running speed (exercise intensity) to the output unit 74. Examples of an output aspect include vibration, sound, light, an image, numerical value display, and the like.

The output unit 74 performs an output in accordance with control of the output control unit 73. Furthermore, the output unit 74 may output the estimated result to other devices (for example, a host computer and the like).

Figure 9:
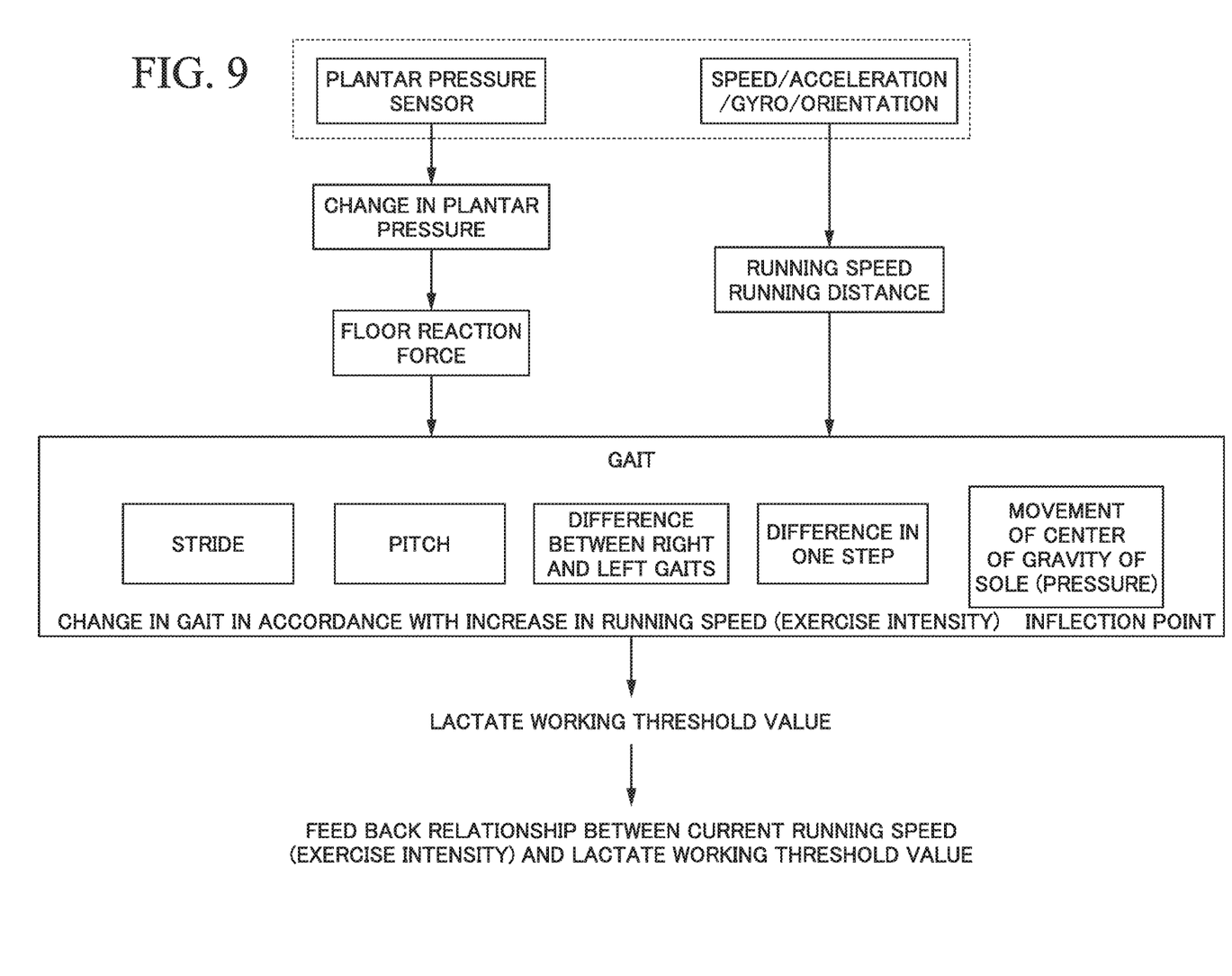
FIG. 9 is a diagram explaining specific processing of the estimating device 7.

FIG. 9 is a diagram explaining specific processing of the estimating device 7.

The estimating unit 72 converts the acquired pressure information into a floor reaction force. Furthermore, the estimating unit 72 detects a running speed and a moving distance on the basis of the motion information. For example, it is possible to obtain a floor reaction force by installing the pressure sensors 1 to 3 in insoles of socks or shoes and measuring a pressure distribution of the sole. A time parameter of a gait such as a contact time from the foot landing to the foot leaving the ground is obtained on the basis of a chronological change of pressure. Moreover, the estimating unit 72 acquires a characteristic amount concerning a gait, for example, a stride, a pitch, a difference between right and left gaits, a difference for each step, and a plantar pressure distribution and the like including a center of gravity of the sole, and the like on the basis of a floor reaction force, a running speed, a moving distance, and the like and estimates a lactate working threshold value on the basis of a change point of the characteristic amount. For example, as illustrated in FIG. 2A, the estimating unit 72 estimates a running speed in which an increase width of a stride is a threshold value or less, that is, a running speed indicating a change point of an increase width of a stride, as the lactate working threshold value. Furthermore, for example, as illustrated in FIG. 2B, the estimating unit 72 estimates a running speed in which an increase width of a pitch is a threshold value or more, that is, a running speed indicating a change point of an increase width of a pitch, as the lactate working threshold value. In addition, for example, as illustrated in FIG. 3, the estimating unit 72 estimates the lactate working threshold value on the basis of a decrease in a difference between right and left gaits or a decrease in dispersion of a parameter of a gait, on the difference between right and left gaits and a fluctuation of a value for each step.

After that, the estimating unit 72 outputs the estimated result and information indicating movement having an intensity with a relationship between the estimated result and a current running speed, that is, whether a current running speed is the lactate working threshold value, is lower than the lactate working threshold value, or higher than the lactate working threshold value, to the output control unit 73. The output control unit 73 feeds back the information output from the estimating unit 72 to the testee or the observer by outputting the information to the output unit 74.

According to the estimating device 7 configured as described above, it is possible to estimate a lactate working threshold value in a state close to an actual movement environment. To be specific, the estimating device 7 calculates a characteristic amount from temporal/spatial parameters of walking/running, movement, work, and an energy metabolism state on the basis of time series information on a floor reaction force and acceleration obtained from the wearable sensors (the pressure sensors 1 to 3 and the motion sensor 5) configured to continuously measure a gait in an unconstrained manner and estimates the lactate working threshold value of the testee on the basis of the calculated characteristic amount. Thus, it is possible to estimate output power at the time of walking or running without using a measuring device such as an ergometer and a power meter. Furthermore, a blood sample for measuring a blood lactate value is unnecessary. For this reason, it is possible to estimate the lactate working threshold value in a state close to an actual movement environment.

Also, the estimating device 7 estimates a lactate working threshold value on the basis of at least one of information of a plantar pressure and a floor reaction force during running. In order to estimate the lactate working threshold value from a gait during running, it is desirable to continuously measure the gait in an unconstrained manner. Although various measuring methods can be used for measuring a gait, particularly regarding to a plantar pressure and a floor reaction force, a change in running in the vicinity of an output of running (work or movement load) and the lactate working threshold value appears in a measured value. Thus, it is possible to measure the lactate working threshold value on the basis of at least one piece of information of the plantar pressure and the floor reaction force. In addition, the estimating device 7 may estimate the lactate working threshold value using a plantar pressure and a floor reaction force estimated on the basis of other biological signals and sensor information. For example, a plantar pressure or a floor reaction force may be estimated on the basis of a signal intensity of an electromyogram of a lower limb so that the lactate working threshold value is estimated on the basis of the plantar pressure or the floor reaction force, or a plantar pressure or a floor reaction force may be estimated on the basis of information of a motion sensor installed on a body so that the lactate working threshold value is estimated on the basis of the plantar pressure or the floor reaction force.

Also, the estimating device 7 feeds back an interrelationship concerning whether an exercise intensity of a current running is the same as, higher than, or lower than the lactate working threshold value of the testee to the testee or the observer through vibration, sound, light, an image, numeral value display, and the like. Thus, the testee can find out whether his/her own current exercise intensity is appropriate or inappropriate. For this reason, the testee can maintain running with an appropriate pace distribution by adjusting the exercise intensity and avoid failures such as stalling due to an over pace.

Also, the estimating device 7 estimates a lactate working threshold value on the basis of at least one characteristic amount among a stride, a pitch, a foot/ground contact time, transition of a plantar pressure distribution, a difference between right and left gaits, and dispersion of each parameter for each step of a gait in movement such as running. As described above, running is optimized during running at an exercise intensity in the vicinity of the lactate working threshold value and the gait changes. As a result, a characteristic amount concerning the gait such as a stride, a pitch, and a foot/ground contact time changes at an exercise intensity with the lactate working threshold value. Furthermore, it is observed that a difference between floor reaction forces of right and left legs, the dispersion of each parameter for each step, and the like, which have an individual difference tend to decrease through the above-described optimization. It is possible to identify the lactate working threshold value on the basis of the characteristics of these data. In addition, it is possible to identify a threshold value from the characteristics in which a trajectory of a center (center of gravity) of a pressure of the sole in a ground contact phase changes in the vicinity of the lactate working threshold value. Furthermore, in a region in which an exercise intensity exceeding the lactate working threshold value is significantly high, the exercise intensity (running speed) is further increased while the above-described optimization reaches its limit. Thus, an increase in pitch, shortening of a foot/ground contact time, and the like are observed. For this reason, it is also possible to estimate the lactate working threshold value through such detection of the characteristics.

It should be noted that the estimating device 7 may estimate the lactate working threshold value on the basis of a combination of amounts of characteristics including a stride, a pitch, a foot/ground contact time, a plantar pressure distribution, a difference between right and left gaits, dispersion of each parameter for each step, and the like. It is possible to estimate the lactate working threshold value of a target person by estimating the lactate working threshold value on the basis of a combination of amounts of characteristics with higher precision.

Also, in the embodiment, a pressure sensor is installed on at least one place of a heel portion, the ball of the foot, and the lateral ball of the foot of the testee. A distribution of a force exerted on the sole along with the movement of a center of gravity of a body and the movement of the feet between heel landing and tiptoe leaving a floor, moves from the heel portion and the lateral ball of the foot toward the ball of the foot and the toes. It is possible to analyze a change in pressure of the sole by performing measurement at any place of the ball of the foot, particularly, from the heel portion and the lateral ball of the foot. Particularly, ascertaining of pressure transfers in a forward/rearward direction through estimation of pressures or forces of two places, i.e., the heel portion and the ball portion of the foot, is important for gait analysis. In addition, ascertaining of pressure transfers in a horizontal direction (inside and outside) and a forward/rearward direction by measuring pressures at three places including the lateral ball of the foot to which the pressures are applied is most desirable for detecting the gait which changes in the vicinity of a lactate working threshold value. A portion whose pressure is measured is not limited to the above description and other regions of the sole such as the toes, a plantar arch, and a portion between the lateral ball of the foot and the ball of the foot may be included.

Modified Example

Although explanation has been mainly provided during running in the above-described embodiment, the estimating device 7 can also be applied during walking such as a walking race.

Although a constitution in which the estimating device 7 estimates a lactate working threshold value of the testee using the pressure information acquired from the pressure sensors 1 to 3 and the motion information acquired from the motion sensor in the above-described embodiment has been illustrated, the present invention need not necessarily be limited thereto. For example, the estimating device 7 may estimate the lactate working threshold value using a biological signal such as an electromyogram and a biological tissue internal pressure (for example, information on an electromyogram of a foot) in addition to the pressure information and the motion information. In this case of a constitution configured in this way, a biological sensor configured to measure a biological signal is installed on the testee. In this case, the estimating device 7 may estimate the lactate working threshold value on the basis of a plantar pressure or a characteristic amount in a biological signal in accordance with a change in speed or exercise intensity of walking movement or running movement. In estimating the lactate working threshold value on the basis of the change in gait described above, there is a clear correspondence such as an exercise intensity of the testee, that is, the exercise intensity rises as running speed increases on a horizontal road. A method of performing measurement on a gait while increasing a running speed stepwise for each certain time (or section) and recording the above-described parameters and characteristic amount associated with the lactate working threshold value is effective for measuring the lactate working threshold value. That is to say, through a method in which an exercise intensity is gradually increased from a state having a low exercise intensity, it is possible to measure an exercise intensity when the lactate working threshold value is reached (or exceeded) using a running speed as a reference.

This method may include adding an increase or increase rate of inclination angle intensity in addition to a running speed for the above-described analysis, for example, using a titled road (uphill road), a stairway, or a tilted treadmill as well as a horizontal road.

As described above, through a method in which an exercise intensity is gradually decreased from a state having a high exercise intensity, an exercise intensity at the time when the lactate working threshold value is reached (or exceeded) may be measured using a running speed as a reference.

Also, the estimating device 7 may record a time when a set goal place has been passed, set automatic stop of measurement or a standby state of a machine in accordance with an arrival of a set time or a set distance, or determine walking stop by disappearance of a sensor response due to walking, on the basis of sensor information.

Also, an optical type marker may be installed on the testee in addition to the motion sensor 5.

The pressure sensors and the force gauge have a limited response speed because the detection of an amount of deflection is used. An increase in pitch and a rapid fluctuation of a pressure along with an increase in running speed cause measurement errors. Furthermore, a drift or a sensitivity decrease of the pressure sensors occurs due to long-distance running, rapid heel ground contact, and the like and increases errors. In addition, an installation position of a sensor moves from an installation place of the sole due to running and the sensitivity decreases and a response changes. In order to correct such errors, the estimating device 7 may be configured so that any of carrying out of calibration with the sensitivity correction along with a running speed change, sensitivity correction along with positional movement or adaptation of a correction value of a response curve, and carrying out of correction from a temporal/spatial interrelationship between measured values of a plurality of measurement places is performed. Furthermore, an auxiliary sensor for calibration may be installed on the testee.

While the embodiment of the present invention has been described in detail above with reference to the drawings, the specific constitution is not limited to this embodiment and designs and the like are also included without departing from the gist of the present invention.

INDUSTRIAL APPLICABILITY

According to the present invention, it is possible to estimate a lactate working threshold value in a state close to an actual movement environment.

REFERENCE SIGNS LIST

1, 2, 3 Pressure sensor
4 Transmitter
5 Motion sensor
6 Receiving device
7 Estimating device
71 Acquiring unit
72 Estimating unit
73 Output control unit
74 Output unit

The invention claimed is:

1. A lactate working threshold-estimating device, comprising:
    at least one memory configured to store instructions; and
    at least one processor configured to execute the instructions to;
    acquire information on a gait of a person whose lactate working threshold value is to be estimated from a sensor installed on the person; and
    estimate the lactate working threshold value of the person on the basis of the acquired information,
    wherein the at least one processor is configured to execute the instructions to:
        estimate, when increasing exercise intensity during walking movement or during running movement, the exercise intensity at which an amount of increase in a stride with increasing the exercise intensity is less than or equal to a first threshold value or the exercise intensity at which an amount of increase in pitch with increasing the exercise intensity is greater than or equal to a second threshold value, as the lactate working threshold value of the person; and
        estimate, when decreasing the exercise intensity during the walking movement or during the running movement, the exercise intensity at which an amount of decrease in the stride with decreasing the exercise intensity is greater than or equal to a third threshold value or the exercise intensity at which an amount of decrease in the pitch with decreasing the exercise intensity is less than or equal to a fourth threshold value, as the lactate working threshold value of the person.

2. The lactate working threshold-estimating device according to claim 1, wherein the at least one processor is further configured to execute the instructions to perform at least one of a correcting a fluctuation in sensitivity of the sensor and an adjusting for a measuring range of a pressure.

3. The lactate working threshold-estimating device according to claim 1, wherein the at least one processor is further configured to execute the instructions to acquire information indicating an interrelationship between the estimated lactate working threshold value and a current or previous exercise intensity and output the acquired information indicating the interrelationship for feedback to at least the person.

4. The lactate working threshold-estimating device according to claim 1, wherein the at least one processor is configured to acquire a chronological change of pressure based on sensor information obtained by a plurality of sensors, and acquire information on the gait of the person, including the stride or the pitch, on the basis of the acquired chronological change of the pressure.

5. A lactate working threshold-estimating method, comprising:
    acquiring information on a gait of a person whose lactate working threshold value is to be estimated from a sensor installed on the person; and
    estimating the lactate working threshold value of the person on the basis of the acquired information,
    wherein the estimating of the lactate working threshold value comprises:
        estimating, when increasing exercise intensity during walking movement or during running movement, the exercise intensity at which an amount of increase in a stride with increasing the exercise intensity is less than or equal to a first threshold value or the exercise intensity at which an amount of increase in pitch with increasing the exercise intensity is greater than or equal to a second threshold value, as the lactate working threshold value of the person; and
    estimating, when decreasing the exercise intensity during the walking movement or during the running movement, the exercise intensity at which an amount of decrease in the stride with decreasing the exercise intensity is greater than or equal to a third threshold value or the exercise intensity at which an amount of decrease in the pitch with decreasing the exercise intensity is less than or equal to a fourth threshold value, as the lactate working threshold value of the person.

* * * * *